(12) United States Patent
Taniguchi et al.

(10) Patent No.: US 6,890,520 B2
(45) Date of Patent: May 10, 2005

(54) THERMALLY STABLE FERULIC ACID DERIVATIVES

(75) Inventors: Hisaji Taniguchi, Ito-gun (JP); Eisaku Nomura, Wakayama (JP); Asao Hosoda, Gobo (JP); Takuo Tsuno, Ito-gun (JP); Yuko Maruta, Ito-gun (JP)

(73) Assignees: Wakayama Prefecture, Wakayama Prefecture (JP); Tsuno Food Industrial Co., Ltd., Wakayama Prefecture (JP)

( * ) Notice: Subject to any disclaimer, the term of this patent is extended or adjusted under 35 U.S.C. 154(b) by 46 days.

(21) Appl. No.: 10/358,183

(22) Filed: Feb. 5, 2003

(65) Prior Publication Data

US 2004/0152912 A1 Aug. 5, 2004

(51) Int. Cl.[7] ............ A61K 7/44; A61K 7/00; A61K 31/05; C07C 69/76; A01N 25/00
(52) U.S. Cl. ............ 424/59; 424/60; 424/78.02; 424/400; 424/401; 514/731; 514/845; 560/51; 560/55; 560/57
(58) Field of Search .......... 424/59, 60, 78.02, 424/400, 401; 514/731, 845; 560/51, 55, 57

(56) References Cited

U.S. PATENT DOCUMENTS 3,600,357 A * 8/1971 Stewart et al. ............ 528/191
5,288,902 A * 2/1994 Taniguchi et al. .......... 562/478
5,552,135 A * 9/1996 Cioca et al. ................ 424/59
5,688,991 A * 11/1997 Taniguchi et al. .......... 560/55

FOREIGN PATENT DOCUMENTS

JP      64-13016 A    1/1989
WO   WO 02/083625   * 10/2002

OTHER PUBLICATIONS

ITE Letters, vol. 2, No. 6, (2001) pp. 51–54, Feb. 6, 2002.

* cited by examiner

*Primary Examiner*—Bernard Dentz
*Assistant Examiner*—Taylor V Oh
(74) *Attorney, Agent, or Firm*—Birch, Stewart, Kolasch & Birch, LLP

(57) ABSTRACT

A ferulic acid derivative represented by the general formula (1); a process for preparing a ferulic acid derivative represented by the general formula (1), comprising reacting ferulic acid or an ester thereof represented by the general formula (2) with a dihalomethane represented by the general formula $CH_2X_2$, wherein X is a halogen atom; and an ultraviolet light-absorbent composition comprising the ferulic acid derivative. Since the ultraviolet light absorbent composition is not only excellent in the ultraviolet light absorption but also very stable against heat, the ultraviolet light absorbent composition can be suitably used as cosmetics which especially require long-term stability.

4 Claims, 5 Drawing Sheets

THERMALLY STABLE FERULIC ACID DERIVATIVES

BACKGROUND OF THE INVENTION

1. Field of the Invention

The present invention relates to a novel ferulic acid derivative and a process for producing the ferulic acid derivative, and an ultraviolet light-absorbent composition comprising the ferulic acid derivative.

2. Discussion of the Related Art

Ferulic acid and an ester thereof are useful compounds because these compounds can absorb ultraviolet light in the UV-A region and the UV-B region which are harmful for human bodies (Japanese Patent Laid-Open No. Sho 64-13016). However, since the ferulic acid and an ester thereof undesirably decompose at a relatively low temperature (176° C., in the case of ferulic acid), its application range is limited when ferulic acid is used for an ultraviolet light-absorbent composition. For instance, if ferulic acid is contained in a plastic by kneading, the temperature of the system in the course of kneading may in some cases become higher than the decomposition temperature for ferulic acid, thereby making it difficult to contain ferulic acid in the plastic with maintaining its ultraviolet light absorption. Furthermore, since ferulic acid does not have sufficient long-term stability, its utilization to cosmetics has been also difficult.

The present invention has been studied in view of the above problems, and an object of the present invention is to provide a thermally stable ferulic acid derivative with maintaining the excellent ultraviolet light absorption of ferulic acid and an ester thereof, and a process for preparing the ferulic acid derivative.

Another object of the present invention is to provide an ultraviolet light-absorbent composition comprising the thermally stable ferulic acid derivative mentioned above.

These and other objects of the present invention will be apparent from the following description.

SUMMARY OF THE INVENTION

As a results of intensive studies in order to solve the above-mentioned problems, the present inventors have found that a thermally stable ferulic acid derivative can be prepared by reacting a ferulic acid or an ester thereof with a dihalomethane. The present invention has been accomplished thereby.

According to the present invention, there is provided:
(I) a ferulic acid derivative represented by the general formula (1):

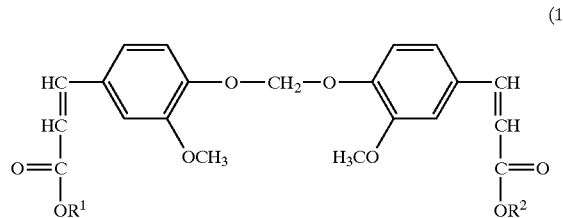

(1)

wherein each of $R^1$ and $R^2$ is independently hydrogen atom or an alkyl group having 1 to 12 carbon atoms;
(II) a process for preparing the ferulic acid derivative represented by the general formula (1) described in item (I) above, comprising reacting a ferulic acid or an ester thereof represented by the general formula (2):

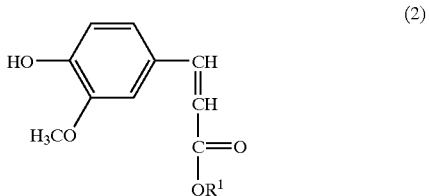

(2)

wherein $R^1$ is as defined above, with a dihalomethane represented by the general formula $CH_2X_2$, wherein X is a halogen atom; and
(III) an ultraviolet light-absorbent composition comprising the ferulic acid derivative represented by the general formula (1) described in (I) above.

DETAILED DESCRIPTION OF THE INVENTION

Figure 1:
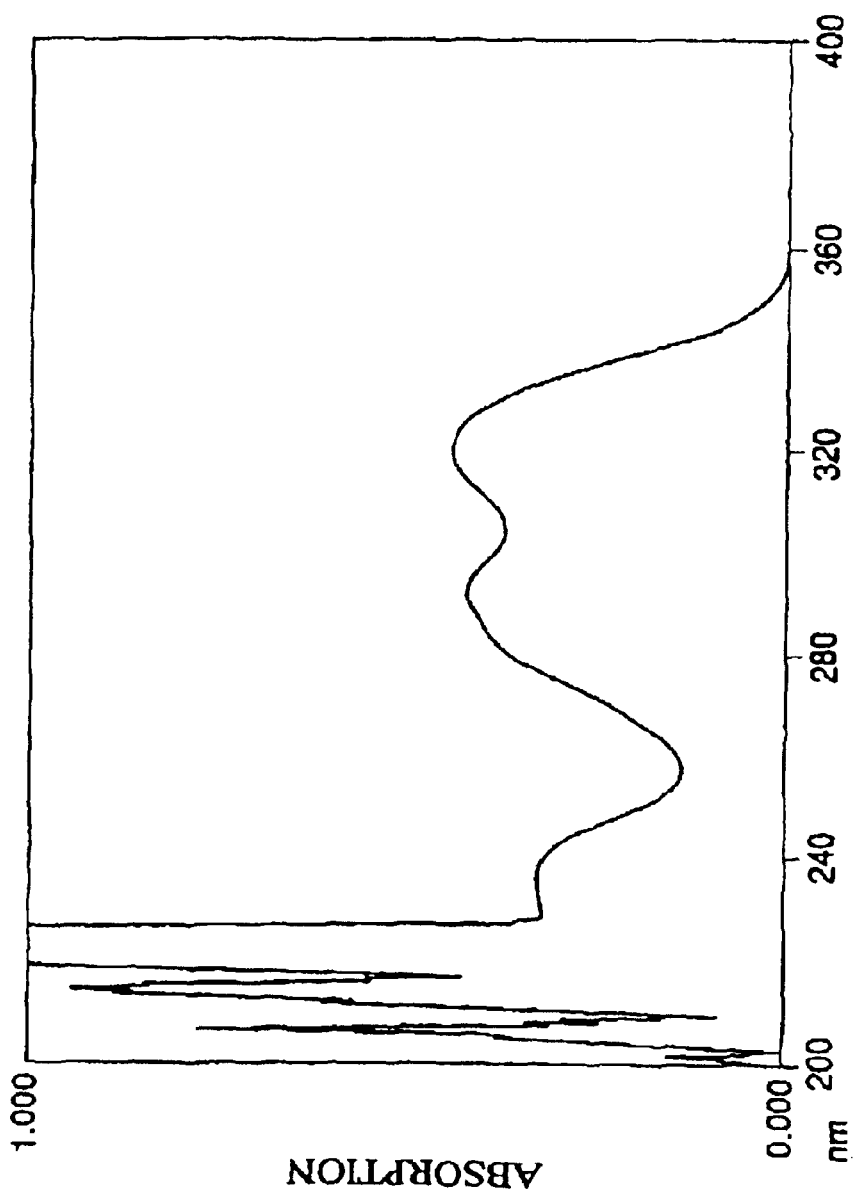
FIG. 1 is an ultraviolet light absorption spectrum of bis-4,4'-(2-ethoxycarbonyl-1-ethenyl)-2,2'-methoxyphenoxymethane prepared in Example 1.

The ferulic acid derivative represented by the general formula (I) of the present invention will be described in detail.

In the general formula (1), each of $R^1$ and $R^2$ is hydrogen atom or an alkyl group having 1 to 12 carbon atoms.

The alkyl group having 1 to 12 carbon atoms represented by $R^1$ or $R^2$ includes linear, branched and cyclic alkyl groups. Concrete examples of the alkyl group represented by $R^1$ or $R^2$ include linear, branched and cyclic alkyl groups having up to 12 carbon atoms, such as methyl, ethyl, an alkyl group having 3 carbon atoms (n-propyl, isopropyl and cyclopropyl), an alkyl group having 4 carbon atoms (n-butyl, isobutyl, sec-butyl, tert-butyl and cyclobutyl), an alkyl group having 5 carbon atoms (n-amyl, isoamyl, sec-amyl, active amyl (2-methylbutyl), tert-amyl and cyclopentyl), an alkyl group having 6 carbon atoms (for instance, n-hexyl, 1-methylpentyl, 2-methylpentyl, cyclohexyl, and the like), an alkyl group having 7 carbon atoms (for instance, n-heptyl, 2-methylhexyl, and the like), an alkyl group having 8 carbon atoms (for instance, n-octyl, 2-ethylhexyl, and the like), and the like. These alkyl groups can have a substituent as long as the substituent would not inhibit the activity of the ultraviolet light-absorbent composition of the present invention. The substituent which may be owned by the alkyl group includes a halogen atom, amino group, sulfonyl group and the like.

The alkyl group represented by $R^1$ or $R^2$ has from 1 to 12 carbon atoms, preferably from 1 to 8 carbon atoms, from the viewpoints of easy preparation (yield or the like), easy handling, thermal stability and the like of the compound represented by the general formula (1).

The present inventors anticipate that the ferulic acid derivatives of which $R^1$ or $R^2$ is an alkyl group having more than 12 carbon atoms have ultraviolet light absorption. However, the compound having the general formula (1) having such an alkyl group is thought to be impractical for use from the viewpoints of yield during the preparation, handling, thermal stability and the like.

In the general formula (1), each of $R^1$ and $R^2$ is independently selected, and it is preferable that $R^1$ and $R^2$ are the same group from the viewpoint of easiness in the preparation of the compound having the general formula (1).

Each of double bonds of the carbon atom bonded to each of —$COOR^1$ and —$COOR^2$ of the general formula (1) with its adjacent carbon atom may be either in the trans-form or the cis-form. Here, those in trans-form and those in cis-form are in equilibrium state under certain conditions, and cis-form is usually converted to trans-form with the passage of a long period of time. Therefore, an isolation of only cis-form is usually difficult. In addition, as explained below, the compound having the general formula (1) of the present invention can be prepared by using ferulic acid contained in rice bran as a starting raw material. The ferulic acid contained in rice bran is in a trans-form.

The process for preparing the compound represented by the general formula (1) of the present invention will be described.

The compound represented by the general formula (1) of the present invention can be prepared by using ferulic acid or an ester thereof represented by the above general formula (2) as a starting raw material.

In the compound having the general formula (2), which is the starting raw material, ferulic acid in which $R^1$ is hydrogen atom is a known compound and commercially available. An ester of ferulic acid in which $R^1$ is an alkyl group having 1 to 12 carbon atoms is also a known compound. In addition, these esters can be prepared by esterification of ferulic acid in accordance with the method described in a literature, or the like. As one of such examples, ferulic acid extracted from rice bran in accordance with the methods described in U.S. Pat. No. 5,688,991, Japanese Patent No. 2095088 and Japanese Examined Patent No. Hei 7-78032 is esterified in accordance with the methods described in Japanese Patent Laid-Open Nos. Hei 9-40613 and Hei 10-130203, whereby an ester of ferulic acid can be easily prepared.

The compound represented by the general formula (1) of the present invention can be prepared by reacting a ferulic acid or an ester thereof represented by the general formula (2), with a dihalomethane represented by the general formula $CH_2X_2$, wherein X is a halogen atom such as chlorine atom, bromine atom or iodine atom.

It is desired that the amount of the dihalomethane used can be usually adjusted to 10 to 50 times by mol, preferably 20 to 35 times by mol, per mol of the compound represented by the general formula (2).

The reaction of the compound represented by the general formula (2) with the dihalomethane can be usually carried out under alkali conditions in the presence of a catalyst.

As the catalyst, there can be used a substituted or unsubstituted crown ether such as 18-crown-6 or dibenzo-18-crown-6; a halogen-substituted alkylphosphonium such as tetramethylphosphonium bromide or triphenylmethylphosphonium iodide; a halogen-substituted alkylammonium such as benzyltrimethylammonium chloride or tetrabutylammonium bromide; and the like.

The amount of the catalyst varies depending upon the catalyst used. It is desired that the amount of the catalyst is usually from 0.1 to 1 mol, preferably from 0.5 to 1 mol per one mol of the compound represented by the general formula (2), which is the starting raw material.

The alkali is not particularly limited, as long as the reaction solution in the system is adjusted to be alkaline. As the alkali, there can be used an alkali metal carbonate such as potassium carbonate or sodium carbonate; an alkali metal hydroxide such as potassium hydroxide or sodium hydroxide; or the like.

It is desired that the amount of alkali is usually equimolar to the compound represented by the general formula (2) which is the starting raw material.

It is desired that the reaction temperature and time can be usually room temperature (15° to 40° C.) and from several to 24 hours, which may vary depending upon the kinds of $R^1$ or $R^2$ in the resulting compound having the general formula (1).

The progress of the reaction can be observed by gas chromatography (GC), high-performance liquid chromatography (HPLC) or the like, and the termination point of the reaction can be confirmed by the disappearance of the raw material.

After the termination of the reaction, the resulting compound represented by the general formula (1) can be collected by, for instance, ordinary separation and purification procedures such as filtration, concentration, extraction and recrystallization.

Incidentally, a compound having the general formula (1) in which $R^1$ and $R^2$ are different can be obtained by reacting a mixture of ferulates having different alkyl groups, such as a mixture of methyl ferulate and ethyl ferulate with a dihalomethane. In this case, three kinds of compounds are generated, and each of the compounds can be easily separated by an ordinary separation procedure such as column chromatography.

The compound represented by the general formula (1) of the present invention is in the form of white solid, crystal or viscous liquid at ambient temperatures. The solid or crystal is hardly soluble in water, and easily soluble in an organic solvent such as toluene, hexane, chloroform or acetone, or a mixed solvent thereof. Therefore, when the compound represented by the general formula (1) of the present invention is applied to various manufactured articles, the compound can be directly added, or a solution prepared by adding the compound to the above-mentioned organic solvent can be added.

The compound represented by the general formula (1) of the present invention has ultraviolet light absorption. The ultraviolet light absorption spectrum of the compound represented by the general formula (1) of the present invention has absorption range at 260 to 370 nm, and shows two absorption peaks near 320 nm and near 290 nm, as shown in Test Examples 1 and 4 set forth below (corresponding to FIGS. 1 and 4). Therefore, the ultraviolet light-absorbent composition of the present invention shows excellent absorption for ultraviolet light in both the A-region and the B-region.

The present invention provides an ultraviolet light-absorbent composition comprising the compound represented by the general formula (1) as an active ingredient by utilizing the ultraviolet light absorption of the compound represented by the general formula (1) of the present invention.

The ultraviolet light-absorbent composition of the present invention can be used as an ultraviolet light absorption-giving manufactured article such as fibers and resins giving ultraviolet light absorption, and as other various manufactured articles. The compound represented by the general formula (1) of the present invention is thermally stable, and its decomposition temperature exceeds 300° C. The ultraviolet light-absorbent composition of the present invention can be especially applied to a manufactured article which can be exposed in high-temperature surroundings utilizing the thermal stability of the compound having the general formula (1). For instance, the compound represented by the general formula (1) of the present invention can be contained by kneading into a plastic. The compound represented by the general formula (1) of the present invention contained by kneading into the plastic can act as a light stabilizer for preventing deterioration by light.

The amount of the compound having the general formula (1) in the ultraviolet light-absorbent composition of the present invention is not particularly limited, as long as the ultraviolet light absorption can be exhibited. In one example, when the ultraviolet light-absorbent composition is kneaded into a resin such as polyvinyl chloride, the compound having the general formula (1) can be added in an amount of 1 to 10 g to 1 kg of the resin.

In addition, there are provided cosmetics comprising a compound represented by the general formula (1) as the ultraviolet light-absorbent composition. Since the compound represented by the general formula (1) has an excellent long-term stability, the compound can also be suitably used for cosmetics.

Components other than the ferulic acid derivative contained in the cosmetics of the present invention are exemplified by various cosmetic components ordinarily used as the base material or the additives in cosmetics without being particularly limited thereto. The components include, for instance, solid, semi-solid or liquid oil agents such as natural animal or plant fats and oils, semi-synthetic fats and oils, hydrocarbon oils, higher fatty acids, higher alcohols, ester oils, silicone oils and fluorine-containing oil agents; water; alcohols such as lower alcohols, sugar alcohols, and sterols; water-soluble polymers such as plant-derived polymers such as gum arabic and traganth, microorganism-derived polymers such as xanthan gum and dextran, starch-based polymers such as carboxymethyl starch, and cellulose polymers such as sodium salt of carboxymethyl cellulose; surfactants such as various anionic, cationic, nonionic and amphoteric surfactants; oil-soluble gelation agents such as metal soap, dextrin fatty acid esters, and sucrose fatty acid esters; inorganic powders such as titanium oxide, magnesium carbonate, mica and hydroxyapatite; organic powders such as polyamide powder; colored pigments; pearl pigments; moisturizing agents; anticorrosive agents; pH adjusting agents; chelating agents; refrigerants; anti-inflammatory agents; cosmeticizing agents such as skin whitening agents, cell activators and blood circulation accelerators; vitamins; perfume; and the like.

The content of the compound represented by the general formula (1) in the cosmetics of the present invention differs depending upon the form or application of the cosmetics. The content of the compound is not particularly limited as long as the ultraviolet light absorption by the ferulic acid derivative of the present invention is exhibited. The content of the compound in the cosmetics of the present invention is preferably from 0.1 to 15% by weight, more preferably from 1 to 10% by weight.

The form of the cosmetics of the present invention is not particularly limited. The form includes, for instance, liquid, milky lotion, gel, paste, cream, and the like. Also, the application of the cosmetics is not particularly limited. There can be suitably used as sun oil, sun-care cream, sun-screen lotion, hair spray, liquid foundation, anti-wrinkle essence, eau de cologne, after-shaving lotion and the like.

The ultraviolet light absorbent composition comprising the compound represented by the formula (1) of the present invention is not only excellent in the ultraviolet light absorption but also very stable against heat. Therefore, the ultraviolet light absorbent composition can be suitably used as cosmetics which especially require long-term stability.

EXAMPLES

The present invention will be describe more specifically by means of the following Examples, without intending to limit the scope or spirit of the present invention thereto.

Example 1

Preparation of Bis-4,4'-(2-ethoxycarbonyl-1-ethenyl)-2,2'-methoxyphenoxymethane

A three-neck flask was charged with ethyl ferulate (2.22 g, 0.01 mol), potassium carbonate (1.38 g, 0.01 mol) and 18-crown-6 (0.005 mol), and 30 mL of dichloromethane was added thereto. The mixture was stirred at 40° C. for 24 hours. After the reaction, the reaction mixture was poured into ice-water in order to remove inorganic substances. The desired compound was extracted with toluene. The organic solution was dried over anhydrous magnesium sulfate to remove water, and thereafter the solvent was distilled off under reduced pressure, to give a colorless solid. This solid was recrystallized from toluene/hexane, to give colorless crystals in prism form.

The crystals had the following properties:

m. p.: 107.4° C., thermal decomposition point: 359° C. (see Test Example 2 set forth below and FIG. 2)t.

IR (KBr): 2977, 2877, 1715, 1630, 1600, 1240 cm$^{-1}$.

$^1$H-NMR (DMSO-$d_6$): δ 1.264 (t, 6H, 2×$CH_3$), 3.820 (s, 6H, 2×$CH_3$), 4.188 (q, 4H, 2×$CH_2$), 5.867 (s, 2H, $OCH_2O$), and 6.5–7.6 ppm (m, 10H, 2×Arom & 2×CH=CH).

$^{13}$C-NMR (CDCl$_3$): δ 14.309, 55.861, 60.431, 92.433, 110.588, 117.004, 117.225, 121.963, 129.820, 144.116, 147.739, 150.043 and 167.001 ppm.

Calculated Value for $C_{25}H_{28}O_8$: C, 65.78; H, 6.18. Found Value: C, 65.62; H, 6.26.

Examples 2 to 8

The same procedures as in Example 1 were carried out except that a catalyst and its amount as shown in the following Table 1 was used in the reaction of Example 1, to give bis-4,4'-(2-ethoxycarbonyl-1-ethenyl)-2,2'-methoxyphenoxymethane. The yield for each Example is shown in Table 1. Table 1 also shows the yield for Example 1.

TABLE 1

Preparation of bis-4,4'-(2-ethoxycarbonyl-1-ethenyl)-2,2'-methoxyphenoxymethane

| Example No. | Catalyst | Catalyst/Ester[b] | Reaction Time | Yield (%) |
|---|---|---|---|---|
| 1 | 18-Crown-6 | 0.5 | 24 hours | 100 |
| 2 | 18-Crown-6 | 0.2 | 24 hours | 11 |

TABLE 1-continued

Preparation of bis-4,4'-(2-ethoxycarbonyl-1-ethenyl)-2,2'-methoxyphenoxymethane

| Example No. | Catalyst | Catalyst/Ester[b] | Reaction Time | Yield (%) |
|---|---|---|---|---|
| 3 | MTPB[c] | 0.1 | 24 hours | 12 |
| 4 | MTPB | 0.2 | 24 hours | 26 |
| 5 | MTPB | 0.5 | 24 hours | 100 |
| 6 | MTPB | 1.0 | 24 hours | 100 |
| 7 | BTMAC[d] | 0.2 | 24 hours | 19 |
| 8 | BTMAC | 0.5 | 24 hours | 70 |

Note:
[a] Ethyl ferulate (2.22 g, 0.01 mol), $K_2CO_3$ (1.38 g, 0.01 mol), $CH_2Cl_2$ (20 mL), temperature: 40° C.
[b] molar ratio
[c] tetramethylphosphonium bromide
[d] benzyltrimethylammonium chloride

Example 9

Preparation of Bis-4,4'-(2-2-ethyl-1-hexyloxycarbonyl-1-ethenyl)-2,2'-methoxyphenoxymethane

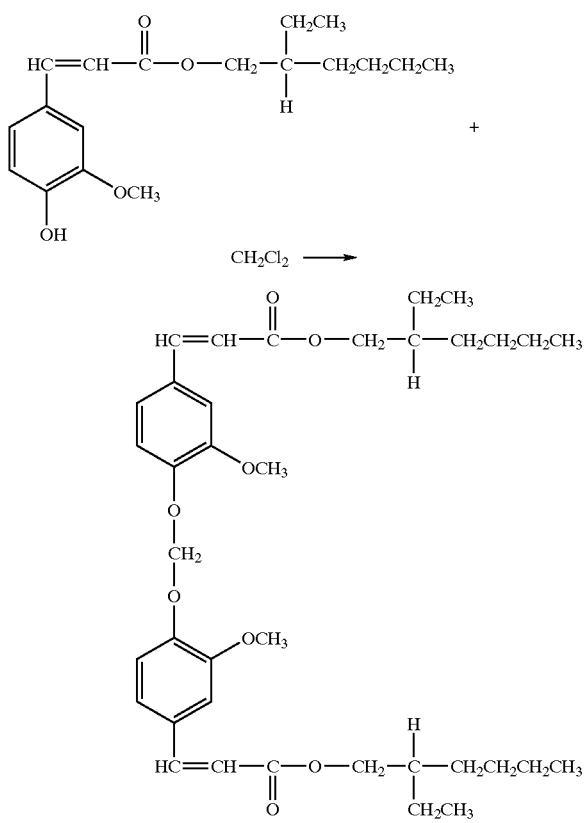

In a three-neck flask, purified 2-ethyl-1-hexyl ferulate (0.996 g, 0.00326 mol) was dissolved in 20 mL of dichloromethane, and potassium carbonate (0.45 g, 0.00326 mol) and 18-crown-6 (0.431 g, 0.0016 mol) were added thereto. The mixture was kept at 40° C. and stirred for 24 hours. After the 24-hour reaction, the reaction mixture was subjected to thin-layer chromatography with n-hexane/ethyl acetate (2:1) as an eluent. As a result, a single spot was confirmed (Rf value of the raw material: 0.62, Rf value of the product: 0.67). After cooling the mixture to room temperature, the cooled mixture was washed three times with 100 mL of distilled water. Next, the mixture was dried over anhydrous magnesium sulfate to remove water, and the obtained mixture was concentrated with an evaporator and a vacuum pump (0.869 g). The resulting concentrate was subjected to thin-layer chromatography with n-hexane/ethyl acetate (2:1) as an eluent. As a result, the Rf value of the product was 0.57 (Rf value of the raw material: 0.69).

In order to confirm the structure of the resulting reaction product, the reaction product was subjected to $^1$H-NMR analysis.

As a result of the $^1$H-NMR analysis, it was found that crown ether remained in the reaction product. Therefore, the reaction product was subjected to column purification using Wako Gel C-300 in a stationary phase, and n-hexane-ethyl acetate (5:1) in a mobile phase, and an effluent was collected in about 10 mL portions. The effluent was subjected to thin-layer chromatography [eluent: n-hexane/ethyl acetate (5:1)] to collect only a fraction having Rf value of 0.26. The collected fraction was concentrated with an evaporator and a vacuum pump (0.762 g).

The yield was 75.04%, and a colorless, viscous oil was obtained.

The resulting product had the following properties: thermal decomposition point: 355° C. (see Test Example 3 set forth below and FIG. 3).

IR (KBr): 3005, 2931, 1713, 1254 $cm^{-1}$.

$^1$H-NMR (DMSO-$d_6$): δ 0.871–1.617 (m, 30H), 3.858 (s, 6H, 2×$CH_3$), 4.10 (t, 4H, 2×$CH_2$), 5.784 (s, 2H, $OCH_2O$), and 6.3–7.6 ppm (m, 10H, 2×Arom & 2 (CH=CH).

Example 10

Preparation of Bis-4,4'-(2-dodecyloxycarbonyl-1-ethenyl)-2,2'-methoxyphenoxymethane

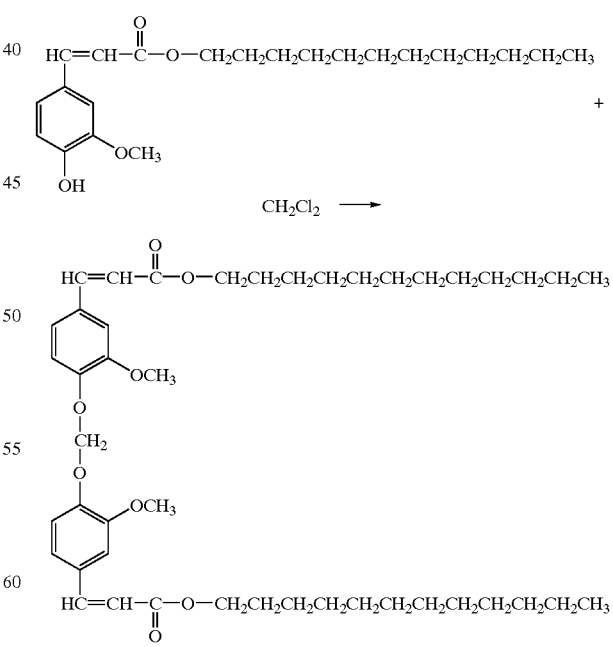

in a three-neck flask, purified dodecyl ferulate (1.005 g, 0.00286 mol) was dissolved in 20 mL of dichloromethane, and potassium carbonate (0.38 g, 0.00286 mol) and 18-crown-6 (0.365 g, 0.0014 mol) were added thereto. The mixture was kept at 40° C. and stirred for 24 hours. After the 24-hour reaction, the reaction mixture was subjected to thin-layer chromatography with n-hexane/ethyl acetate (2:1) as an eluent. As a result, a single spot was confirmed (Rf value of the raw material: 0.21, Rf value of the reaction mixture: 0.28). After cooling the mixture to room temperature, the mixture was washed three times with 100 mL of distilled water. Next, the mixture was dried over anhydrous magnesium sulfate to remove water, and the obtained mixture was concentrated with an evaporator and a vacuum pump (0.869 g). The resulting concentrate was subjected to thin-layer chromatography with n-hexane/ethyl acetate (2:1) as an eluent. As a result, the Rf value of the concentrate was 0.69 (Rf value of the raw material: 0.6).

The yield was 85.69%, and a white solid was obtained.

In order to confirm the structure of the resulting reaction product, the reaction product was subjected to $^1$H-NMR analysis.

The resulting product had the following properties: m. p.: 71.2° C., thermal decomposition point: 318° C. (see Test Example 5 set forth below and FIG. 5).

IR (KBr): 3008, 2941, 2854, 1709, 1635, 1585, 1254 cm$^{-1}$.

$^1$H-NMR (DMSO-d$_6$): δ 0.840–1.678 (m, 46H), 3.856 (s, 6H, 2×CH$_3$), 4.188 (t, 4H, 2×CH$_2$), 5.792 (s, 2H, OCH$_2$O), 6.3–7.6 ppm (m, 10H, 2×Arom & 2×CH=CH).

Test Example 1

An ultraviolet light absorption spectrum of bis-4,4'-(2-ethoxycarbonyl-1-ethenyl)-2,2'-methoxyphenoxymethane prepared in Example 1 in a 95% ethanol solution was obtained by using Model U-2001 Double-Beam Spectrophotometer (commercially available from Hitachi Ltd.).

The spectrogram is shown in FIG. 1.

Test Example 2

A thermal decomposition temperature of bis-4,4'-(2-ethoxycarbonyl-1-ethenyl)-2,2'-methoxyphenoxymethane prepared in Example 1 was determined by using a thermogravimetric-differential thermal simultaneous analyzer "TG/DTA 6200" (commercially available from Seiko Instruments Inc.).

Figure 2:
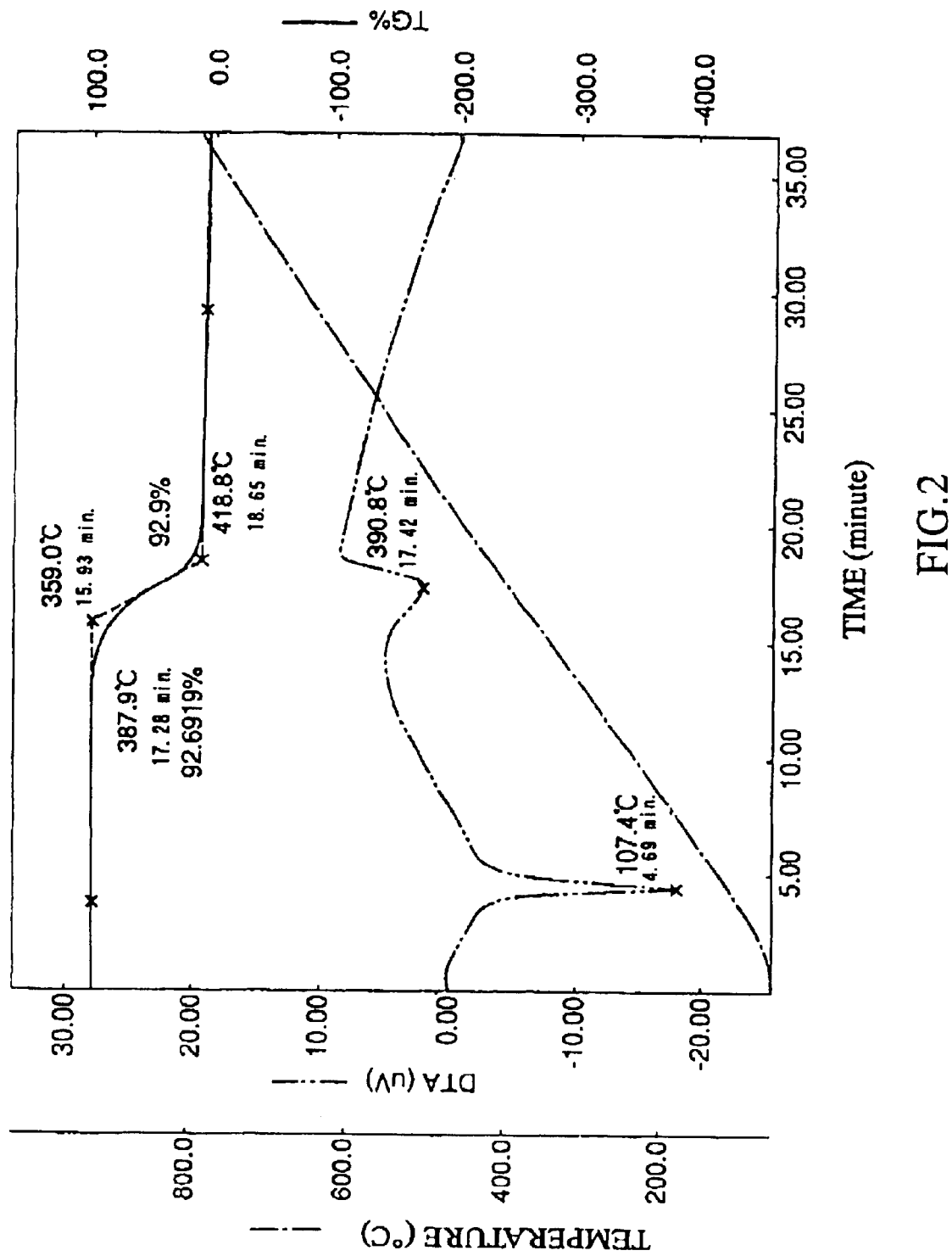
FIG. 2 is a thermal decomposition curve of bis-4,4'-(2-ethoxycarbonyl-1-ethenyl)-2,2'-methoxyphenoxymethane prepared in Example 1.

The thermal decomposition curve is shown in FIG. 2.

Test Example 3

A thermal decomposition temperature of bis-4,4'-(2-2-ethyl-1-hexyloxycarbonyl-1-ethenyl)-2,2'-methoxyphenoxymethane prepared in Example 9 was determined by using a thermogravimetric-differential thermal simultaneous analyzer "TG/DTA 6200" (commercially available from Seiko Instruments Inc.).

Figure 3:
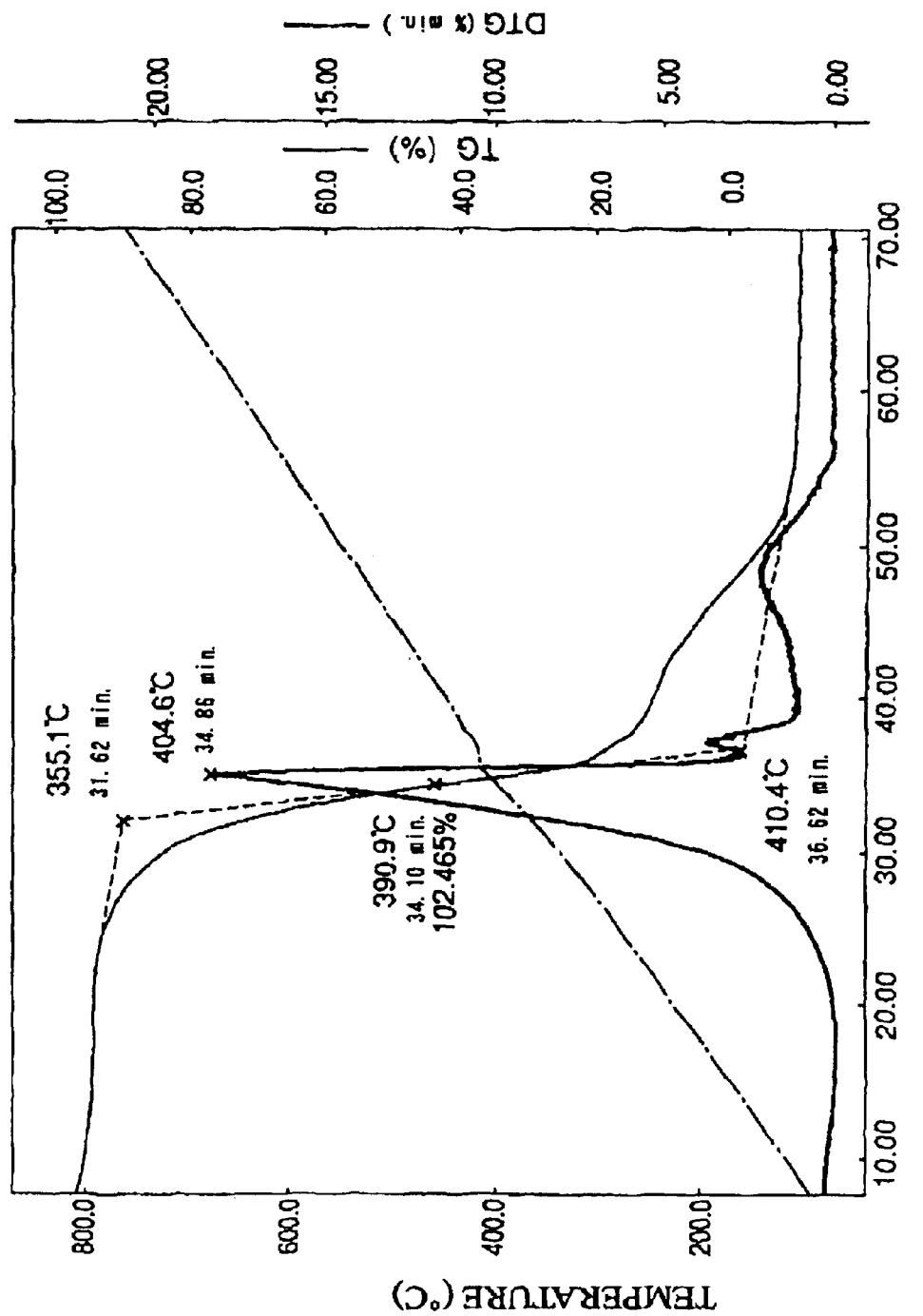
FIG. 3 is a thermal decomposition curve of bis-4,4'-(2-2-ethyl-1-hexyloxycarbonyl-1-ethenyl)-2,2'-methoxyphenoxymethane prepared in Example 9.

The thermal decomposition curve is shown in FIG. 3.

Test Example 4

An ultraviolet light absorption spectrum of bis-4,4'-(2-dodecyloxycarbonyl-1-ethenyl)-2,2'-methoxyphenoxymethane prepared in Example 10 in a 95% ethanol solution was obtained by using Model U-2001 Double-Beam Spectrophotometer (commercially available from Hitachi Ltd.).

Figure 4:
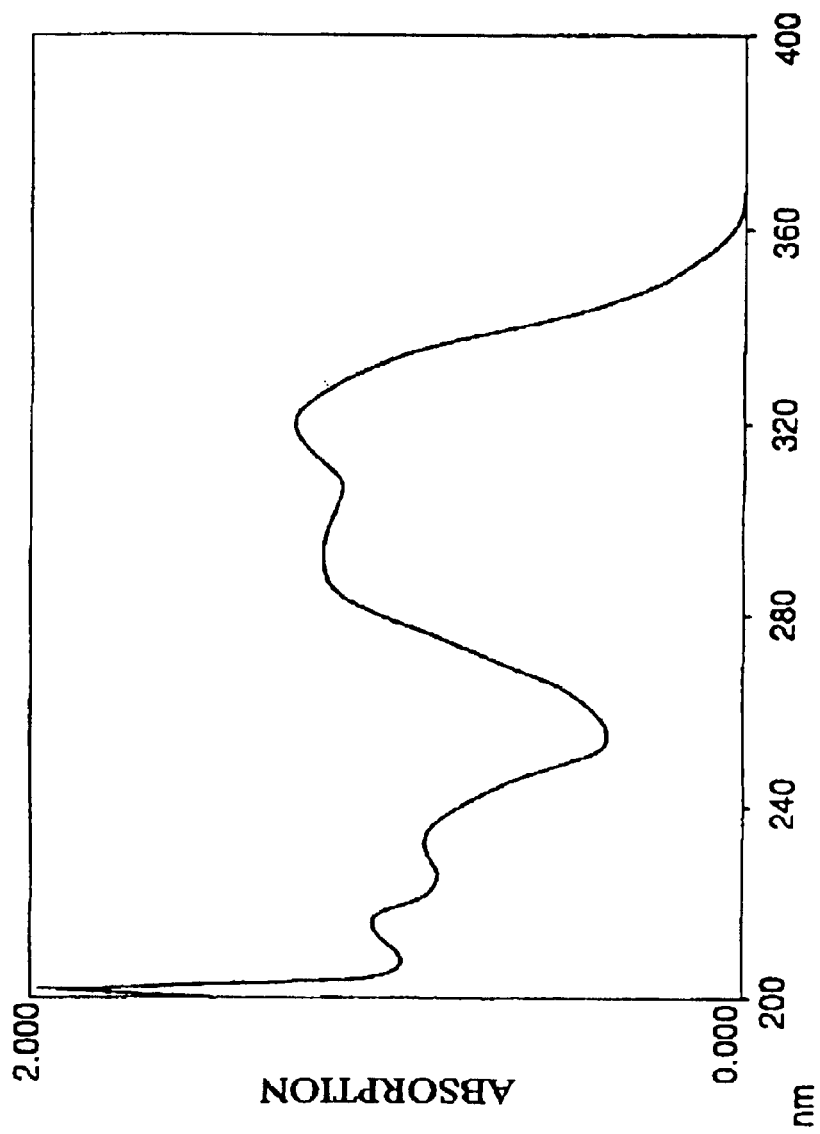
FIG. 4 is an ultraviolet light absorption spectrum of bis-4,4'-(2-dodecyloxycarbonyl-1-ethenyl)-2,2'-methoxyphenoxymethane prepared in Example 10.

The spectrogram is shown in FIG. 4.

Test Example 5

A thermal decomposition temperature of bis-4,4'-(2-dodecyloxycarbonyl-1-ethenyl)-2,2'-methoxyphenoxymethane prepared in Example 10 was determined by using a thermogravimetric-differential thermal simultaneous analyzer "TG/DTA 6200" (commercially available from Seiko Instruments Inc.).

Figure 5:
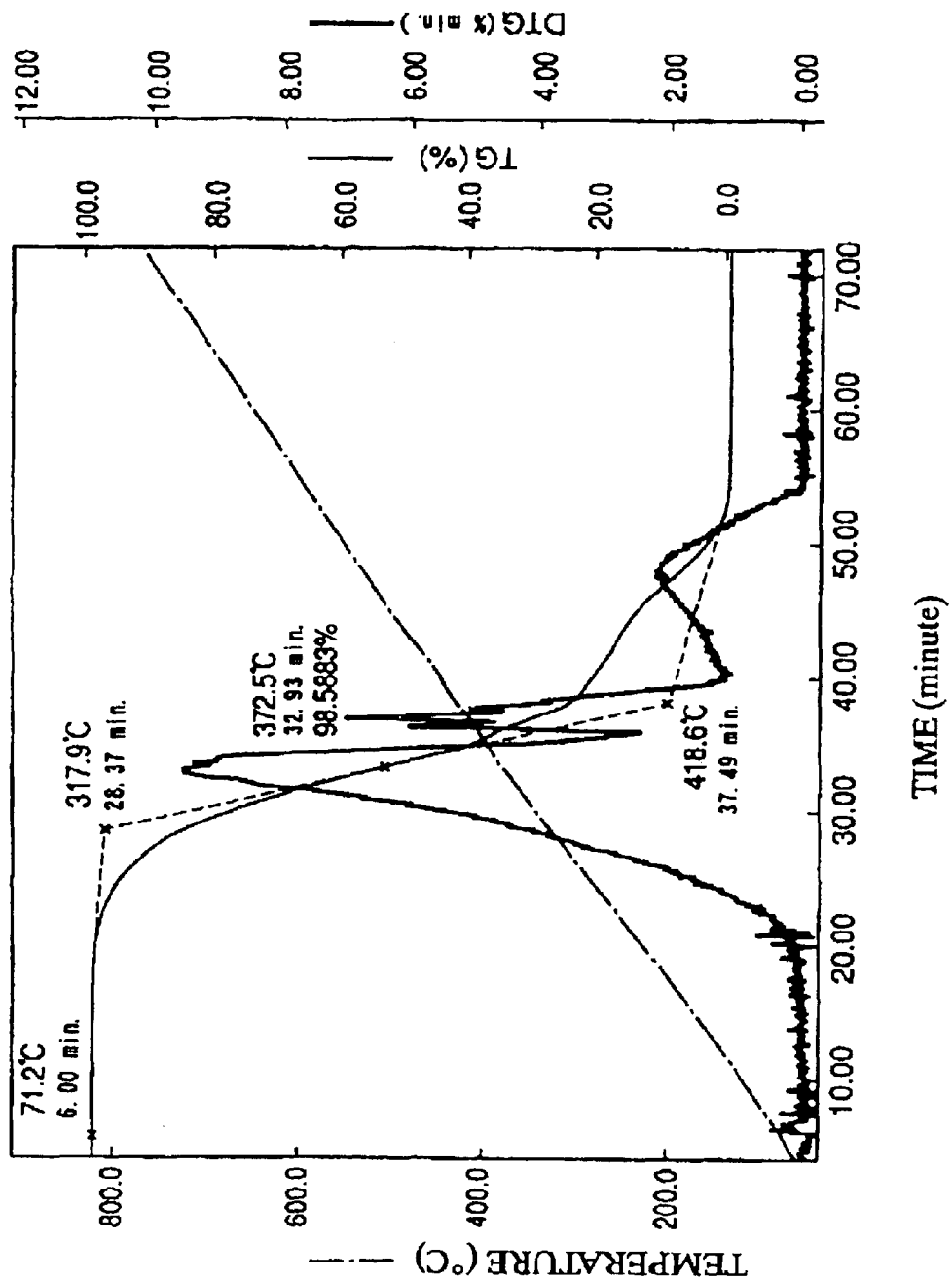
FIG. 5 is a thermal decomposition curve of bis-4,4'-(2-dodecyloxycarbonyl-1-ethenyl)-2,2'-methoxyphenoxymethane prepared in Example 10.

The thermal decomposition curve is shown in FIG. 5.

Example 11 [Preparation of Cosmetics]

1) Preparation Example of Sun Oil

| Composition | | Weight/Weight (%) |
|---|---|---|
| Component 1. | Bis-4-4'-(2-ethoxycarbonyl-1-ethenyl)-2,2'-methoxyphenoxymethane Prepared in Example 1 | 10.0 |
| Component 2. | Liquid Paraffin | 74.88 |
| Component 3. | Isopropyl Myristate | 10.0 |
| Component 4. | Palm Oil | 5.0 |
| Component 5. | Natural Vitamin E | 0.02 |
| Component 6. | Perfume | 0.10 |

Preparation Process

Components 1 to 6 were sequentially added at room temperature, and the components were sufficiently stirred to dissolve, to give a sun oil.

2) Preparation Example of Sun-Care Cream

| Composition | | Weight/Weight (%) |
|---|---|---|
| Component 1. | Purified Water | 54.08 |
| Component 2. | 1,3-Butylene Glycol | 7.0 |
| Component 3. | Methyl Paraoxybenzoate | 0.3 |
| Component 4. | Triethanolamine | 1.0 |
| Component 5. | Titanium Dioxide | 3.0 |
| Component 6. | Bis-4,4'-(2-ethoxycarbonyl-1-ethenyl)-2,2'-methoxyphenoxymethane Prepared in Example 1 | 10.0 |
| Component 7. | Liquid Paraffin | 10.0 |
| Component 8. | Vaseline | 5.0 |
| Component 9. | Cetanol | 3.0 |
| Component 10. | Stearic Acid | 3.0 |
| Component 11. | Lipophilic Glycerol Monostearate | 3.0 |
| Component 12. | Dimethyl Polysiloxane | 0.5 |
| Component 13. | Natural Vitamin E | 0.02 |
| Component 14. | Perfume | 0.1 |

Preparation Process

Each of an aqueous phase composed of Components 1 to 5 and an oil phase composed of Components 6 to 13 was heated to 80° C. and dissolved. In the aqueous phase, Component 5 was sufficiently dispersed, and then the oil phase was added to the aqueous phase, and the mixture was emulsified with high-speed agitation. The resulting emulsion was cooled, and Component 14 was added and evenly mixed, to give a sun-care cream.

3) Preparation Example of Sun-Screen Lotion

| Composition | | Weight/Weight (%) |
|---|---|---|
| Component 1. | Purified Water | 70.78 |
| Component 2. | 1,3-Butylene Glycol | 7.0 |
| Component 3. | Methyl Paraoxybenzoate | 0.3 |
| Component 4. | Hydroxyethyl Cellulose | 0.3 |
| Component 5. | Bis-4,4'-(2-ethoxycarbonyl-1-ethenyl)-2,2'-methoxyphenoxymethane Prepared in | 10.0 |

-continued

| Composition | | Weight/Weight (%) |
|---|---|---|
| Example 1 | | |
| Component 6. | Sorbitan Monooleate | 1.0 |
| Component 7. | POE(10)Oleyl Ether | 1.0 |
| Component 8. | Isopropyl Myristate | 5.0 |
| Component 9. | Vaseline | 3.0 |
| Component 10. | Cetanol | 1.0 |
| Component 11. | Dimethyl Polysiloxane | 0.5 |
| Component 12. | Natural Vitamin E | 0.02 |
| Component 13. | Perfume | 0.1 |

Preparation Process

Each of an aqueous phase composed of Components 1 to 4 and an oil phase composed of Components 5 to 12 was heated to 80° C. and dissolved. In the aqueous phase, Component 4 was sufficiently dissolved with swelling, and then the oil phase was added to the aqueous phase, and the mixture was emulsified with high-speed agitation. The resulting emulsion was cooled, and Component 13 was added and evenly mixed, to give a sun-screen lotion.

4) Preparation Example of Hair Spray

| Composition | | Weight/Weight (%) |
|---|---|---|
| Component 1. | Alkanolamine Solution of Acrylic Resin | 10.0 |
| Component 2. | Oleyl Alcohol | 0.1 |
| Component 3. | Methylphenyl Polysiloxane | 0.2 |
| Component 4. | Bis-4,4'-(2-ethoxycarbonyl-1-ethenyl)-2,2'-methoxyphenoxymethane Prepared in Example 1 | 1.0 |
| Component 5. | Ethanol | 88.5 |
| Component 6. | Perfume | 0.2 |

Preparation Process

Components 1 to 4 and 6 were sequentially added to Component 5, and the components were dissolved with sufficient stirring. Using the resulting solution as the stock solution, 50% by volume of a stock solution and 50% by volume of dimethyl ether were packed with gas, to give a hair spray.

5) Preparation Example of Liquid Foundation

| Composition | | Weight/Weight (%) |
|---|---|---|
| Component 1. | Purified Water | 54.58 |
| Component 2. | 1,3-Butylene Glycol | 10.0 |
| Component 3. | Bentonite | 0.5 |
| Component 4. | POE(10) Sorbitan Monostearate | 1.0 |
| Component 5. | Triethanolamine | 1.0 |
| Component 6. | Methyl Paraoxybenzoate | 0.3 |
| Component 7. | Talc | 3.1 |
| Component 8. | Titanium Dioxide | 5.1 |
| Component 9. | Red Oxide | 0.4 |
| Component 10. | Yellow Iron Oxide | 1.4 |
| Component 11. | Black Iron Oxide | 0.1 |
| Component 12. | Bis-4,4'-(2-ethoxycarbonyl-1-ethenyl)-2,2'-Methoxyphenoxymethane Prepared in Example 1 | 10.0 |
| Component 13. | Stearic Acid | 2.5 |
| Component 14. | Lipophilic Glycerol Monostearate | 2.8 |
| Component 15. | Liquid Paraffin | 8.0 |
| Component 16. | Natural Vitamin E | 0.02 |
| Component 17. | Perfume | 0.1 |

Preparation Process

A dispersion of Component 3 in Component 2 was added to Component 1, and the mixture was mixed at 80° C. with high-speed agitation. Components 4 to 6 were added to the mixture, and then sufficiently agitated, to give an aqueous phase. A mixture prepared by adding Components 7 to 11 with sufficiently mixing and pulverizing was added to the resulting aqueous phase, and the resulting mixture was sufficiently agitated at 80° C. Next, to the resulting mixture was added a solution prepared by dissolving Components 12 to 16 with heating at 80° C., and mixed with high-speed agitation. After the mixture was cooled, Component 17 was added and evenly mixed, to give a liquid foundation.

6) Preparation Example of Anti-Wrinkle Essence

| Composition | | Weight/Weight (%) |
|---|---|---|
| Component 1. | Purified Water | 65.18 |
| Component 2. | 1,3-Butylene Glycol | 8.0 |
| Component 3. | Methyl Paraoxybenzoate | 0.3 |
| Component 4. | Triethanolamine | 1.0 |
| Component 5. | Bis-4,4'-(2-ethoxycarbonyl-1-ethenyl)-2,2'-Methoxyphenoxymethane Prepared in Example 1 | 10.0 |
| Component 6. | POE(10)Cetyl Ether | 2.0 |
| Component 7. | Lipophilic Glycerol Monostearate | 2.0 |
| Component 8. | Stearic Acid | 3.0 |
| Component 9. | Cetanol | 1.0 |
| Component 10. | Liquid Paraffin | 5.0 |
| Component 11. | Soft Cholesterin Lanoline Fatty Acid | 2.0 |
| Component 12. | Vitamin E Acetate | 0.2 |
| Component 13. | Natural Vitamin E | 0.02 |
| Component 14. | Placenta Extract | 0.2 |
| Component 15. | Perfume | 0.1 |

Preparation Process

Each of an aqueous phase composed of Components 1 to 4 and an oil phase of Components 6 to 13 was dissolved at 80° C. with heating. The oil phase was added to the aqueous phase, and the mixture was emulsified with high-speed agitation. After the resulting emulsion was cooled, Components 14 and 15 were added thereto, and evenly mixed, to give an anti-wrinkle essence.

7) Preparation Example of Eau de Cologne

| Composition | | Weight/Weight (%) |
|---|---|---|
| Component 1. | Ethanol | 80.0 |
| Component 2. | Perfume | 4.0 |
| Component 3. | POE(10) Cured Castor Oil | 1.0 |
| Component 4. | Bis-4,4'-(2-ethoxycarbonyl-1-ethenyl)-2,2'-Methoxyphenoxymethane Prepared in Example 1 | 1.0 |
| Component 5. | Purified Water | 14.0 |

Preparation Process Components 2 to 4 were added to Component 1 and dissolved. To the resulting mixed solution was added Component 5, and the container was tightly sealed, and allowed to stand in a cool, dark place for several days. The contents were filtered, to give eau de cologne.

8) Preparation Example of After-Shaving Lotion

| Composition | | Weight/Weight (%) |
|---|---|---|
| Component 1. | Ethanol | 55.0 |
| Component 2. | Dipropylene Glycol | 3.0 |
| Component 3. | POE(10) Cured Castor Oil | 2.0 |
| Component 4. | Bis-4,4'-(2-ethoxycarbonyl-1-ethenyl)-2,2'-Methoxyphenoxymethane Prepared in Example 1 | 1.0 |
| Component 5. | Perfume | 0.1 |
| Component 6. | L-Menthol | 0.05 |
| Component 7. | Purified Water | 38.75 |
| Component 8. | Dipotassium Glycyl Phosphate | 0.1 |

Preparation Process

Components 2 to 6 were sequentially added to Component 1 and dissolved with agitation. To the resulting mixed solution was added a solution prepared by dissolving Component 8 in Component 7, and the mixture was sufficiently stirred, to give after-shaving lotion.

All of the cosmetics (sun oil, sun-care cream, sun-screen lotion, hair spray, liquid foundation, anti-wrinkle essence, eau de cologne and after-shaving lotion) obtained as described above have excellent ultraviolet light absorption. Therefore, by using these cosmetics, influences of ultraviolet light to skin and hair can be effectively reduced.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A ferulic acid derivative represented by the formula (1):

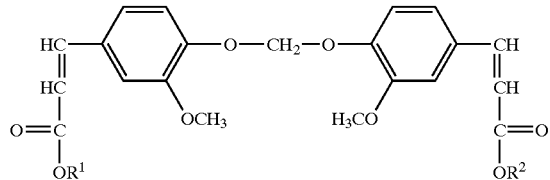

(1)

wherein each of $R^1$ and $R^2$ is independently hydrogen atom or an alkyl group having 1 to 12 carbon atoms.

2. A process for preparing a ferulic acid derivative represented by the formula (1):

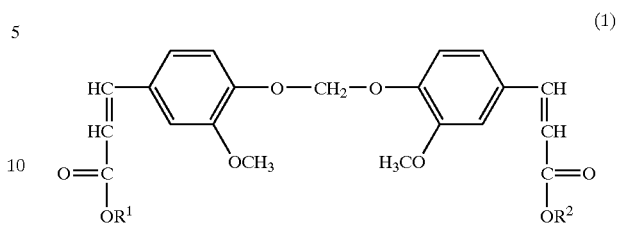

(1)

wherein each of $R^1$ and $R^2$ is independently hydrogen atom or an alkyl group having 1 to 12 carbon atoms, comprising reacting ferulic acid or an ester thereof represented by the general formula (2):

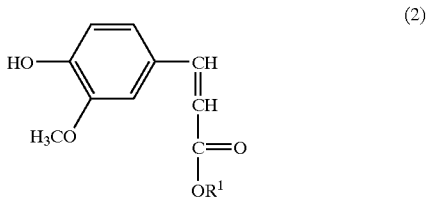

(2)

wherein $R^1$ is as defined above, with a dihalomethane represented by the formula $CH_2X_2$, wherein X is a halogen atom.

3. An ultraviolet light-absorbent composition comprising the ferulic acid derivative of claim 1.

4. The ultraviolet light-absorbent composition according to claim 3, which is cosmetics.

* * * * *